(12) United States Patent
Pettit (10) Patent No.: US 9,632,046 B2
(45) Date of Patent: Apr. 25, 2017

(54) APPARATUS AND METHOD FOR ASSESSING THERMO-MECHANICAL FATIGUE RELATED PHENOMENA WITHIN A TEST MATERIAL

(71) Applicant: Richard G. Pettit, Fruit Heights, UT (US)

(72) Inventor: Richard G. Pettit, Fruit Heights, UT (US)

(73) Assignee: FractureLab LLC, Fruit Heights, UT (US)

( * ) Notice: Subject to any disclaimer, the term of this patent is extended or adjusted under 35 U.S.C. 154(b) by 409 days.

(21) Appl. No.: 14/173,813

(22) Filed: Feb. 5, 2014

(65) Prior Publication Data
US 2015/0219575 A1   Aug. 6, 2015

(51) Int. Cl.
*G01N 25/72*   (2006.01)
(52) U.S. Cl.
CPC .................. *G01N 25/72* (2013.01)
(58) Field of Classification Search
CPC ............. G01N 2203/0073; G01N 3/60; G01N 2203/0005; G01N 2203/0057;
(Continued)

(56) References Cited

U.S. PATENT DOCUMENTS 4,248,094 A * 2/1981 Thompson ................ G01L 1/22
73/760
4,752,140 A * 6/1988 Cielo ...................... G01N 25/72
356/484

(Continued)

OTHER PUBLICATIONS

Aleksander Yevtushenko, Kazimierz Rozniakowski, Malgorzata Rozniakowska, Axi-Symmetrical Transient Temperature Fields and Quasi-Static Thermal Stresses Initiated by a Laser Pulse in a Homogeneous Massive Body, 2011, pp. 58, 70, 76-80, ISBN: 978-953-307-585-3, InTech, Available at http://www.intechopen.com/download/get/type/pdfs/id/20000. Relevance: An application of thermoelastic theory and lasers to metal surface processing and rock fracture (single pulse). p. 77 shows a crack extending from recast region in Fe 3% steel after 35 Joule pulse from Nd:YAG laser.*

(Continued)

*Primary Examiner* — Lisa Caputo
*Assistant Examiner* — Philip Cotey (57) ABSTRACT

The invention pertains to a test apparatus and method for assessing thermo-mechanical fatigue related phenomena within a test material wherein a heat source, such as a laser beam is applied to a specimen consisting of a body of the test material, thereby introducing heat to a primary heat introduction zone on the surface of the body to cause local cyclic heating. As part of the cycle, heat is removed through a portion of the specimen surface sufficiently remote from the heat introduction zone to create a substantially spherical temperature gradient within the specimen resembling that of a point source on a semi-infinite body. A stress gradient results from local thermal expansion, thus thermo-mechanically cycling the material. As a result of the thermo-mechanical cycling, phenomena including thermo-mechanically induced creep, residual stress, changes in physical properties, crack initiation and crack growth may be observed within the material, and evaluated for scientific or engineering purposes. An optional background temperature control feature may also be included to raise the background temperature of the specimen during thermal cycling. Among many useful embodiments described herein, the test method may also be configured for non-destructive use on a component, wherein the local damage or crack growth due to thermal cycling is afterwards removed and the surface blended or otherwise reconditioned as required to restore component functionality and structural integrity.

11 Claims, 8 Drawing Sheets

(58) Field of Classification Search
CPC ... G01N 2203/0064; G01N 2203/0066; G01N 2203/0224; G01N 2203/0262; G01N 2203/027; G01N 25/18; G01N 25/72; G01N 3/32; G01K 11/00
USPC .......................................................... 374/47
See application file for complete search history.

(56) References Cited

U.S. PATENT DOCUMENTS

| | | | | |
|---|---|---|---|---|
| 5,479,259 | A * | 12/1995 | Nakata | G01K 5/52 356/432 |
| 5,587,532 | A * | 12/1996 | Rose | G01N 29/2425 73/571 |
| 5,967,660 | A | 10/1999 | Akpan et al. | |
| 6,935,187 | B1 | 8/2005 | Gorman et al. | |
| 7,559,251 | B2 | 7/2009 | Lee et al. | |
| 2002/0018510 | A1* | 2/2002 | Murphy | G01N 25/72 374/45 |
| 2006/0039443 | A1* | 2/2006 | Watanabe | G01N 25/18 374/44 |
| 2009/0000382 | A1* | 1/2009 | Sathish | G01N 25/72 73/606 |
| 2009/0116533 | A1* | 5/2009 | O'Connell | G01N 29/14 374/5 |
| 2011/0106485 | A1* | 5/2011 | Popov | G01N 25/18 702/136 |

OTHER PUBLICATIONS

Zhiyue Xu, Claude Reed, Richard Parker, Laser Spallation of Rocks for Oil Well Drilling, Proceedings of the 23rd International Congress on Applications of Lasers and Electro-Optics, 2004, p. 1, Laser Institute of America, Available at http://www.ne.anl.gov/facilities.lal/Publications/Laser%20well%20drilling/spallation.pdf. Relevance: An application of thermoelastic theory and lasers to create spallation fractures in rock. (Single cycle, not fatigue).

R. K. Kersey et al, Thermal Mechanical Fatigue Cracks Growth from Laser Drilled Holes in Single Crystal Material, US Air Force Research Laboratory Report AFRL-RX-WP-TP-2012-0251, Mar. 2012. Relevance: Illustration of current, conventional TMF practice.

M. Aischeler, Thermal Fatigue Properties of Polycrystalline Copper in CLIC Accelerating Structures: Surface Roughness and Hardening as a Function of Grain Orientation, 25th Linear Accelerator Conference, Tsubaka, Japan, Sep. 12-17, 2010. Relevance: Key data from this paper summarized in Table 1 of specification as prior art.

Bartosik et al, Lateral gradients of phases, residual stress and hardness in a laser heated Ti0.52Al0.48N coating on hard metal, Surface & Coatings Technology, vol. 206, 2012. Relevance: Key data from this paper summarized in Table 1 of specification as prior art.

Cote et al, Laser Pulse Heating Simulation of Firing Damage on Coated Gun Bore Surfaces, Technical Report ARCCB-TR-01005, Benet Laboratories, 2001. Relevance: Key data from this paper summarized in Table 1 of specification as prior art.

Zhu, Miller, Influence of High Cycle Thermal Loads on Thermal Fatigue Behavior of Thick Thermal Barrier Coatings, ARL-TR-1341, May 1997. Relevance: Key data from this paper summarized in Table 1 of specification as prior art.

Zhu et al, Oxidation- and Creep-Enhanced Fatigue of Haynes 188 Alloy-Oxide Scale System Under Simulated Pulse Detonation Engine Conditions, NASA TM-2002-211484, 2002. Relevance: Key data from this paper summarized in Table 1 of specification as prior art.

Nishinoiri et al, Evaluation of Microfracture Mode in Ceramic Coating during Thermal Cycle Test using Laser AE technique, Materials Transactions, vol. 45, No. 1, 2004. Relevance: Key data from this paper summarized in Table 1 of specification as prior art.

Panda et al, Thermal shock and thermal fatigue study of ceramic materials on a newly developed ascending thermal shock test equipment, Science and Technology of Advanced Materials, vol. 3, 2002. Relevance: Key data from this paper summarized in Table 1 of specification as prior art.

Rymer, Stress Intensity Solutions of Thermally Induced Cracks in a Combustor Liner Hot Spot Using Finite Element Analysis, Dissertation, Georgia Institute of Technology, 2005. Relevance: Key data from this paper summarized in Table 1 of specification as prior art.

Xiang Chen et al, Effects of Hot Compressive Dwell Condition on Fatigue Crack Growth Response of Cast Aluminum Alloys, presented to TMS 2012, 141st Meeting and Exhibition, Mar. 11-15, 2012, Orlando, FL. Relevance: Illustrates analysis method for TMF, but validation testing was done isothermally, due to lack of resources to run true TMF testing.

M. Zecchino, C. R. Forest, Quantifying Laser-Induced Thermal Deformation of a MEMS Device Static and Dynamic Optical Profiling Characterize Heating-Cooling Cycle, www2.veeco.com/pdfs.php/96/?showPDF=true Relevance: A laser induced heating application, thin plate.

M Rehmer et al, Effect of Testing Conditions on Thermal Shock Resistence of Advanced Ceramics, Federal Institute for Materials Research and Testing, Berlin, Germany, http://www.bam.de/de/kompetenzen/fachabteilungen/abteilung_5/fg52/fg52_medien/fg52_poster_27.pdf Relevance: Another thermal shock test using laser heating. Not enough information to add to Table 1 of Specification. Appears to be thin plate application.

S. Caltroni et al, Fatigue Testing of Materials by UV Pulsed Laser Irradiation, presented to 9th European Particle Accelerator Conference, Jul. 5-9, Lucerne, Switzerland, http://accelconf.web.cern.ch/accelconf/e04/PAPERS/MOPLT013.PDF Relevance: Another thermal shock test using laser heating. Appears similar to Aicheler's short pulse work presented in specification, Table 1.

Hong Zhou, Temperature Rise induced by a Rotating or Dithering Laser Beam, Advanced Studies in Theoretical Physics, vol. 5, 2011, No. 10, 443-468. Relevance: A theoretical paper containing analyses potentially of interest with regard to applications described in specification.

* cited by examiner

APPARATUS AND METHOD FOR ASSESSING THERMO-MECHANICAL FATIGUE RELATED PHENOMENA WITHIN A TEST MATERIAL

CROSS-REFERENCE TO RELATED APPLICATIONS

Not Applicable.

BACKGROUND OF THE INVENTION

1. Field of the Invention

The invention pertains to a test apparatus and method for assessing thermo-mechanical fatigue related phenomena within a test material, including but not limited to thermo-mechanically induced creep, residual stress, changes in physical properties, crack initiation and crack growth, occurring at temperatures below the melting temperature of the material.

2. Description of the Prior Art

Thermo-mechanical fatigue (TMF) testing is necessary in elevated temperature engineering applications where component durability and safety concerns merit the associated costs, which are often substantial, due to the difficulty of cycling both thermally and mechanically at the same time. A well-known type of TMF test is performed on a tubular specimen intermittently induction heated and cooled by air running through the tube, while simultaneously being loaded mechanically in strain control in a hydraulic test machine. A recent example of this class of testing is described in *Thermal Mechanical Fatigue Cracks Growth from Laser Drilled Holes in Single Crystal Material*, by Kersey et al (US Air Force Research Laboratory Report AFRL-RX-WP-TP-2012-0251, March 2012). Systems capable of this type of strain-controlled TMF testing are commercially available from well-known test equipment vendors, including specialized units that permit biaxial loading, and internationally recognized standard test methods exist. However, the high cost of the equipment, and the obvious complexities of the method can render it prohibitive.

Another class of TMF testing involves heating a specimen with a thermal gradient, which creates a corresponding passive mechanical stress gradient associated with mismatched thermal expansion. A simple example of an active-thermal, passive-mechanically cycled test used to assess a body of material (though it can also be coated) is described in U.S. Pat. No. 6,935,187 B1, which utilizes a specimen consisting of an elongated base with a fin extending along its length. When thermally cycled in an oven, the thermal lag in the base results in a cyclic thermal mismatch between the base and the fin, resulting in cyclic stresses, which can eventually result in cracks initiating and growing in the fin. While the method is vastly simpler than conventional strain-controlled TMF testing, thermocycling in an oven remains a substantial time and energy-consuming process. Also, the hot-compressive dwell time, an important parameter in TMF testing, is limited by the geometry, and cannot be varied at will because the thermal stresses vanish at steady state conditions.

Many such active-thermal, passive-mechanical test applications focus on the effect of TMF on surface integrity, especially as applied to coatings, including thermal barrier coatings (TBCs)—ceramic coatings used on parts like turbine blades to shield them from high temperature operational environments, and industrial hard coatings for tooling applications. These applications use various heat sources such as a torch, an infrared heater, or a laser beam to heat a surface to create a substantially through-thickness temperature distribution of largely planar geometry. That is, the isotherms in the region of interest are substantially planar, and parallel to each other. A summary of references of this kind are summarized in Table 1. Parameters not provided by authors were estimated or found in the literature. Values in the last three columns will be explained later on.

The relatively planar nature of the thermal distribution can be viewed as a result of one of two mechanisms. In the first, the test resembles a thin plate heated on one side and cooled on the other, naturally approaching a steady-state linear thermal distribution through the thickness, with the planar geometry described. The resulting differential temperature is sensitive to both the thermal flux and the thickness of the plate, and is also strongly influenced by the thermal resistance and variations in cooling rate at the cooling surface. Also, the planar nature of the thermal distribution requires that the size of the heated zone exceed the thickness of the specimen, typically requiring a high power heat source and high energy consumption during the test.

The second mechanism involves heating by heat pulses sufficiently short in duration that they penetrate a small depth into the surface relative to the size of the heated zone before they are substantially dissipated, thus also assuming a planar nature within the penetration depth. Peak temperatures reached are a function of heat flux magnitude and duration, and the thermal diffusivity of the material, but are insensitive to thickness and cooling method as the thickness becomes large compared to the penetration depth. Temperatures near the heated zone vary rapidly during the heating cycle and are of transient character, as this mechanism is not operable at near steady-state conditions.

TABLE 1

Summary of Prior Art with Substantially Planar Thermal Distributions

| Reference | Heat Source, Substrate Material | Thermal Diffusivity $\alpha$ mm²/sec (in²/sec) | Heat Application Zone size d mm (in) | Heating Time $t_h$ (sec) | Radius of Fiducial Hemisphere $r_f$ mm (in) | $\dfrac{d}{\sqrt{\alpha t_h}}$ | $\dfrac{r_f}{d}$ |
|---|---|---|---|---|---|---|---|
| M Aischeler, Thermal Fatigue Properties of Poycrystalline Copper in CLIC Accelerating Structures: Surface Roughness and Hardening as a Function of Grain Orientation, 25th Linear Accelerator Conference, Tsubaka, Japan, 12-17 Sep., 2010. | Pulsed Laser, Copper | 111 (0.172) | 1.26 (0.050) | 4E-08 | 9 (0.354) | 600 | 7.12 |
| Bartosik et al, Lateral gradients of | Continuous- | 35 | 6 | 30 | 5 | 0.19 | 0.83 |

TABLE 1-continued

Summary of Prior Art with Substantially Planar Thermal Distributions

| Reference | Heat Source, Substrate Material | Thermal Diffusivity α mm²/sec (in²/sec) | Heat Application Zone size d mm (in) | Heating Time $t_h$ (sec) | Radius of Fiducial Hemisphere $r_f$ mm (in) | $\dfrac{d}{\sqrt{\alpha t_h}}$ | $\dfrac{r_f}{d}$ |
|---|---|---|---|---|---|---|---|
| phases, residual stress and hardness in a laser heated $Ti_{0.52}Al_{0.48}N$ coating on hard metal, Surface & Coatings Technology, vol. 206, 2012. | Wave laser, WC-Co | (0.054) | (0.236) | | (0.197) | | |
| Cote et al, Laser Pulse Heating Simulation of Firing Damage on Coated Gun Bore Surfaces, Technical Report ARCCB-TR-01005, Benet Laboratories, 2001. | Pulsed Laser, Steel | 10 (0.016) | 2.6 (0.102) | 0.005 | 2.54 (0.100) | 11.6 | 0.98 |
| Zhu, Miller, Influence of High Cycle Thermal Loads on Thermal Fatigue Behavior of Thick Thermal Barrier Coatings, ARL-TR-1341, May 1997. | Pulsed & CW Laser, Steel | 10 (0.016) 10 (0.016) 10 (0.016) | 32 (1.260) 32 (1.260) 32 (1.260) | 0.009 300 1800 | 5.88 (0.231) 5.88 (0.231) 14.7 (0.579) | 107 0.58 0.24 | 0.18 0.18 0.46 |
| Zhu et al, Oxidation- and Creep-Enhanced Fatigue of Haynes 188 Alloy-Oxide Scale System Under Simulated Pulse Detonation Engine Conditions, NASA TM-2002-211484, 2002. | Pulsed & CW Laser, Haynes 188 | 4.8 (0.007) 4.8 (0.007) | 32 (1.260) 32 (1.260) | 1800 0.001 | 1 (0.039) 1 (0.039) | 0.34 462 | 0.03 0.03 |
| Nishinoiri et al, Evaluation of Microfracture Mode in Ceramic Coating during Thermal Cycle Test using Laser AE technique, Materials Transactions, vol. 45, no. 1, 2004. | Infra-red Image Furnace, 304 SS | 4 (0.006) | 10 (0.394) | 180 | 5.8 (0.228) | 0.37 | 0.58 |
| Panda et al, Thermal shock and thermal fatigue study of ceramic materials on a newly developed ascending thermal shock test equipment, Science and Technology of Advanced Materials, Vol. 3, 2002. | Gas Torch, $Si_3N_4$ | 3.5 (0.005) | 13 (0.512) | 20 | 6 (0.236) | 1.55 | 0.46 |
| Rymer, Stress Intensity Solutions of Thermally Induced Cracks in a Combustor Liner Hot Spot Using Finite Element Analysis, Dissertation, Georgia Institute of Technology, 2005. | Gas Torch, B-1900 + Hf | 10 (0.016) | 60 (2.362) | 25 | 1.5 (0.059) | 3.79 | 0.03 |

While a more precise characterization of the operational regimes associated with "thin plate" and "short pulse" modes of operation described above will be given hereafter, a summary of the operational characteristics of these modes is given in Table 2, compared with a "desired state" which identifies some of the objects of the invention to be presented.

TABLE 2

Operability Summary

| Mode of Operation | Operable near steady state | Insensitive to thickness* | Insensitive to cooling method* | Sensitive to thermal flux at heated surface | Energy Consumption |
|---|---|---|---|---|---|
| Thin Plate | Yes | No | No | Yes | High |
| Short Pulse | No | Yes | Yes | Yes | Low |
| Desired State | Yes | Yes | Yes | Yes | Low |

*A minimum thickness may be required to achieve this property.

While in some respects, a planar thermal distribution might seem to make sense for TMF testing of thin coatings—in concept, the thin plate linear thermal distribution is very simple to analyze, and matches the symmetry of a planar coating layer—limitations, such as those identified in Table. 2 can be significant in practice. As alluded to earlier, it is useful to be able to specify a desired thermo-mechanical cycle, often including a dwell time at constant temperature and applied mechanical strain, and then configure the test to approximate that cycle. This would require near-steady-state operability, which is only available in thin plate mode. It is also preferable for the time required to reach near-steady-state conditions to be small compared to the desired dwell times, which may not always be practical with thin plates for short dwell times.

Insensitivity to thickness allows reliable comparison between different specimen configurations, and is often accompanied by insensitivity to cooling methods, but in current practice is only available in the short pulse mode. Panda et al observed a very strong thickness effect in their thin plate data, despite mounting their specimen with a thermally conductive paste to a water-cooled copper pedestal to make sure their cooling was even and reproducible. Bartosik et al used a copper pedestal immersed in a thermally regulated liquid reservoir to control the temperature of their thin plate sample.

In addition to the specimen configurations tested by Zhu et al (2002) listed in Table 1, they apparently took advantage of the thickness independence of the short pulse mode to apply their method to structural components and conventional 4-point bend specimens. They did not give sufficient details to include the component and 4-point bend tests in the table, but they were run with a 0.8 ms heat pulse on various items. It is apparent that they could not run thickness-independent tests with dwell in this manner, thus their dwell tests were run on thin-plate specimens (and thin-plate-like 90 degree angles). It is also worth noting that to obtain the large spot size used (apparently motivated by their thin plate work), they employed a 1500W laser. Use of a less expensive and power consuming device would be desirable.

While most of the laser beams used in the prior art of Table 1 were nominally circular, Aicheller employed a rectangular beam. Cote et al used a fiber-optic cable to transmit the laser beam to the specimen, resulting in a more uniform flux distribution.

Also of interest in the prior art, theoretical thermal and thermo-elastic solutions for numerous potentially relevant heating scenarios are available in the literature. An application of one such solution to the problem of laser rock spallation is described by Xu et al in *Laser Spallation of Rocks for Oil Well Drilling* (Proceedings of the $23^{rd}$ International Congress on Applications of Lasers and Electro-Optics, 2004).

Recently, a creep-shakedown-based TMF crack growth prediction approach has been a topic of study for analysis of the hot-compressive dwell cycle that typically results from active-thermal passive-mechanical TMF cycles, as described in a presentation entitled *Effects of Hot Compressive Dwell Condition on Fatigue Crack Growth Response of Cast Aluminum Alloys* by Xiang Chen et al of the Integrative Material Design Center (IMDC) at Worcester Polytechnic Institute (WPI) (presented to TMS 2012, $141^{st}$ Meeting and Exhibition, Mar. 11-15, 2012, Orlando, Fla.). The method was applied to an aluminum casting material in the context of a cylinder head TMF problem. While the material characterization and analysis method can account for quite general hot-compressive time-dependent behavior in a variable-temperature environment, the partial validation performed utilized an isothermal test method that, while capturing the isothermal creep-related phenomena, could not rule out the possibility of additional non-isothermal effects that might further accelerate the crack. Non-isothermal testing was not performed because WPI lacked the resources to do so, a situation that could be remedied at many academic and industrial institutions if a more accessible means of TMF testing were available. This also suggests that, using the IMDC approach, a creep shakedown model for a given material could be developed and partially validated using simple isothermal testing, with a final validation involving a few non-isothermal TMF tests to prove whether the method properly predicts the more general behavior. Among other applications, the invention now to be discussed could fill this need.

SUMMARY OF THE INVENTION

The invention pertains to a test apparatus and method for assessing thermo-mechanical fatigue related phenomena within a test material. An embodiment is described utilizing a test specimen prepared of a body of the test material, which may include surface treatments of interest according to the purpose of the test. A portion of the surface of the body is designated as the primary heat introduction zone, through which heat is cyclically introduced into the specimen during testing. The finite maximum dimension, d, spanning this zone shall be designated as its size. The zone location is defined by its centroid. The means by which the heat is applied may be described generically as a heat source, but in concept may include a gas torch, an infrared heater, a laser beam, an electron beam, a resistance heater or any other heat source capable of transmitting heat to a localized surface area.

For each thermal cycle, heat is introduced through the primary heat introduction zone, and must also be removed from the specimen. For the present application, it is useful for heat to be removed at a heat removal zone that is broadly distributed and remote. To aid in a discussion of "remoteness" in this context, consider a hemispherical specimen initially at a uniform background temperature $T_o$. At the beginning of a cycle (t=0), a primary heat introduction zone centered on the flat side of the hemisphere is subjected to a constant heat input. As the material heats up the outer spherical boundary is cooled to keep it at its initial temperature $T_o$.

If the size of the primary heat introduction zone is small compared to the specimen size, the transient temperature distribution will, at a scale exceeding the primary heat introduction zone size, closely resemble that of a constant-thermal-power point heat source on a semi-infinite body, which has the known spherically symmetric transient solution $$T(r, t) - T_o = \frac{\text{thermal power input}}{2\pi k r} \text{erfc}\left(\frac{r}{2\sqrt{\alpha t}}\right) \quad (1)$$

Where T(r,t) is the local temperature, $T_o$ is the initial uniform background temperature of the body, r is the distance from the point heat source, t is the time that has elapsed since the thermal power was turned on, k and $\alpha$ are the material thermal conductivity and diffusivity, and erfc( ) is the complimentary error function. For the purposes of this example, after a predetermined heating hold time $t_h$, the heat flow is turned off, and the specimen is allowed time to cool before the cycle repeats. A more broad definition of $t_h$ will be given hereafter.

The complimentary error function term approaches unity for long hold times, revealing a steady state differential temperature (T–$T_o$) that is bounded for all finite r and vanishes with 1/r at infinity (because the primary heat introduction zone will necessarily be of finite size, the infinite temperature predicted at the origin by Equation (1) is of no physical significance). This "boundedness" is a unique attribute of 3D (spherically symmetric) thermal conduction solutions in the infinite or semi-infinite domain. Equivalent 2D (circular symmetry) and 1D (through-thickness) conduction problems (geometries common in prior art) are unbounded everywhere in infinite or semi-infinite domains, and thus do not have steady-state solutions in these domains.

While the finite hemispherical specimen configuration described in this example is cooled at its outer radius to maintain a differential temperature of zero throughout the cycle, the semi-infinite solution predicts zero temperature differential only at infinity. Under otherwise equivalent conditions the semi-infinite solution predicts, at a radius equal to that of the finite hemisphere, a finite differential temperature at the time corresponding to the end of the heating time of the cycle. This boundary differential temperature, normalized to the simultaneous maximum differential temperature in the body near the heat source, is a measure of the deviation of the local thermal distribution of the finite specimen to the corresponding semi-infinite solution. This normalized parameter will be referred to as the Boundary Temperature Ratio (BTR). The BTR may be considered a measure of the spherical "remoteness" of the heat removal zone—lower BTR corresponding to more remote heat removal.

The BTR is also a measure of the sensitivity of the specimen to the way it is cooled, and the temperature stability of the outer boundary. The semi-infinite solution has BTR=0 and has no exterior hemispherical surface to cool; thus for a given material the local thermoelastic response near the heat source is entirely driven by the way heat is applied, and the background temperature $T_o$. The same is largely true for a finite, but low BTR hemispherical specimen, except that the presence of the cooling on the outer spherical boundary permits some control over $T_o$ (more on this later). Observe that if the earlier requirement that the outer spherical boundary be cooled to precisely maintain the initial (ambient) temperature were relaxed to the more practical approach of cooling by ambient natural or forced convection, the thermal cycle of the low BTR specimen would experience a modest increase in mean temperature in proportion to its BTR and the total heat flux, but would otherwise remain unchanged. By comparison, the planar thermal distribution in a thin plate heated from one side and cooled on the other to achieve the same level of thermal gradient, has an infinite (or more precisely, undefined) BTR and is very sensitive to changes in the way it is cooled.

Further, because the outer differential temperature of a low BTR hemispherical specimen would be even lower if the specimen were larger, it follows that adding material to the outer boundary of a low BTR hemispherical specimen results in a specimen geometry with an even lower BTR. Heat removal then takes place through the specimen surface at a location at or beyond the spherical boundary of the original hemisphere.

Re-stated in broader terms, the BTR of a specimen of given size and shape can be conservatively approximated by the BTR of the largest hemispherical region of test material, centered at the centroid of the primary heat introduction zone, which the specimen body substantially includes. The hemisphere so determined shall be referred to as the fiducial hemisphere of the specimen, and the radius of that hemisphere shall be termed the fiducial radius of the specimen, $r_f$.

The definition of the words "substantially includes" in this connection allows for the possibility that the surface of the specimen nominally coinciding with the "flat" side of the fiducial hemisphere may in fact have some irregularity, and that the body of material may in fact include porosity, cavities, holes or recesses that may be important for the test, so long as these voids are either characteristic of the material, or make up a small fraction—no more than 25 percent—of the volume of the fiducial hemisphere. If this criterion is met, the specimen is said to "substantially include" the hemispherical region, even though the hemisphere may in fact extend locally beyond the specimen surface at these irregularities.

An estimate which will hereafter serve as an operational definition of the BTR is obtained in terms of test conditions and material properties using Equation (1) and the following expression $$BTR \cong F_{BTR} \cdot \frac{T(r_f, t_h) - T_o}{T\left(\frac{d}{2}, t_h\right) - T_o} \qquad (2)$$

Where the heating time $t_h$ is interpreted broadly as the duration of a single heat application period as the specimen is thermally cycled. For very complex cycles, or cycles where the heat input is never non-zero, a steady state value ($t_h \rightarrow \infty$) may be conservatively used. The factor $F_{BTR}$ is determined by the shape and heat flux distribution of the primary heat introduction zone, but is generally below 0.65, which corresponds approximately to an annular heating distribution. More typical is the BTR associated with a uniform, constant circular flux distribution applied during the heating portion of the cycle for which $F_{BTR}$=0.5. Concentrating the flux distribution more toward the center of the primary heat introduction zone will tend to decrease the BTR. Narrowing the zone into an ellipse will also tend to decrease the BTR, thus use of $F_{BTR}$=0.5 will be conservative for a wide range of heating scenarios.

The BTR varies inversely with the ratio of the fiducial radius to the primary heat introduction zone size, $r_f/d$. For basic utility, an $r_f/d$ ratio of at least 1.2 is recommended which corresponds to a BTR of roughly 0.2. In many applications, it is often useful to further configure the test to sufficiently large $r_f/d$ ratios to keep the BTR below a predetermined value. In many practical applications, it is useful to operate with BTR below 0.1, and potentially well below this value.

The BTR also varies inversely to the diffusivity ratio, which shall be defined herein as the dimensionless ratio $d/\sqrt{\alpha t_h}$. The radical term in the denominator may be viewed as a measure of the penetration depth associated with the heat cycle, particularly as $t_h$ becomes small. At a diffusivity ratio of approximately ten, the spherically symmetric character of the thermal solution is largely lost, and beyond ten assumes the substantially planar character associated with short pulse operation of the prior art.

As the specimen is cycled through one or more test cycles, it may be monitored and evaluated to assess thermo-mechanical fatigue related phenomena within the test material, including but not limited to thermo-mechanically induced creep, residual stress, changes in physical properties, crack initiation and crack growth. Various sensors common to the art may be used in this evaluation process.

It should also be mentioned at this stage that Equation (1) neglects cooling from the face of the semi-infinite body, which will in practice occur naturally, and if included in the analysis would act to reduce the BTR estimate. Often, a detailed thermo-mechanical analysis of a particular specimen and the applied cycle using theoretical solutions or numerical tools known in the art is performed in connection with a test program to inform experimental design and facilitate interpretation and evaluation of the results. To simplify the assumptions made in such analyses, and further tailor the desired test conditions, it is sometimes useful to apply insulation to a portion of the specimen surface.

To this point in the present discussion, the background temperature $T_o$ at the beginning of each cycle has been determined largely by the coolant temperature, ostensibly at or below ambient. In practice, however, it is useful to specify this lower bound of the temperature cycle to predetermined value, often above ambient. While to some degree both upper and lower local temperatures of the thermal cycle can be controlled by means already described, further utility can be gained by adding means to elevate the background temperature of the specimen. A simple example would be to conduct the entire experiment inside an oven heated to a background temperature selected by the user (raise the ambient temperature). Another example is to apply distributed heat to a portion of the specimen surface or volume substantially beyond the boundary of the fiducial hemisphere by way of a resistance heater, an inductance coil or other heat source. The amount of heat input can be adjusted to control the temperature to a background value at a position remote from the primary heat introduction zone.

Advantages of the basic embodiments already described include the following. First, the use of a substantially spherical thermal profile accommodates near-steady-state operation, which in the planar prior art is only available in thin plate operation, while still maintaining thickness insensitivity, and insensitivity to the mode of cooling, which in the planar prior art is only available in short pulsed operation. This satisfies the "desired state" of operability identified in Table 2. Further, in many practical situations the temperatures in the vicinity of the primary heat introduction zone can attain near steady-state temperatures (and thus near-steady state thermal compressive strains) within a time scale that is small compared to useful hot compressive dwell times. For example, a nickel alloy specimen with a primary heat introduction zone size d=1 mm (0.04 in), the material within a radius of 1 mm (0.04 in) from the centroid of heating would be within 10 percent of steady state stress and temperature values in a transient interval of about six seconds, compared to dwell times of interest on the order of minutes. This provides an opportunity to vary the hot-compressive dwell time merely by changing the period and duration of thermal power delivery. Where smaller dwell times are of interest, the transient interval reduces in proportion to $d^2$, permitting increasingly high frequency cycling with controlled dwell times at smaller primary heat introduction zone sizes.

Second, the local thermoelastic response is easy to regulate for low BTR specimens. The thermoelastic analogue of St. Venant's principle guarantees that local variations in cooling remote from a local heat source will have minimal effect on temperatures and stresses in the vicinity of the heat source. This enables a high degree of control on the local thermoelastic state of interest despite using very simple means of heat removal, including natural convection to ambient air (or other environment as desired), or forced convection, as by use of a fan or air jet. Conduction to a remote heat sink and radiation are also viable means for heat removal, for example, if the test is to take place in a vacuum. The more elaborate means of thermal control developed for thin plate operation in the prior art are not required.

Third, local transient and steady-state temperature distributions are favorably severe near the primary heat introduction zone, thus enabling efficient development of high levels of thermoelastic stress. Like the BTR, this situation improves as the size of the body increases relative to the primary heat introduction zone size, increasing the local constraint.

Fourth, because the portion of the body that is highly heated is limited to a localized region in the vicinity of the primary heat introduction zone, the power consumption, and cost of related capital equipment, tends to be favorably small for many useful configurations, and can be minimized by reducing the primary heat introduction zone size.

Fifth, reduced primary heat introduction zone size also facilitates the formation and investigation of TMF induced crack growth in the so-called "small crack" regime of fracture mechanics, such as where the crack is of the order of the crack tip plastic zone size or a particular microstructural feature of the material, which is mechanistically of interest in the art.

One exemplary means for introducing heat locally when high thermal flux is needed over a small area is to irradiate the surface within the primary heat introduction zone with at least one energy beam, such as a laser or an electron beam. Depending on the application, various means may be useful to control the way in with each beam is applied to the specimen surface, potentially including one or more of the following—means for modulating the power of a beam, such as a beam shutter or a variable amplitude power supply; means such as a beam deflector or articulating mount for directing or articulating a beam (or the specimen relative to a beam) so it heats the desired location within the primary heat introduction zone at the desired time during the cycle; means, such as a lens, to form the size of a beam where it irradiates the surface; and means to form the shape or flux distribution of a beam where it irradiates the surface.

It is also useful to locally contour the shape of the specimen surface in the vicinity of the primary heat introduction zone to a predetermined shape, thereby further tailoring the thermo-mechanical cycle occurring in the material as it is cyclically heated. As mentioned earlier, material removed to make holes, recesses, or other aspects of the desired shape shall constitute a small fraction of the fiducial hemisphere.

With regard to means to form the shape of a beam where it irradiates the surface, optical beam conditioning hardware available in the art permits shaping of the one or more beams used for a given test configuration so that it irradiates the specimen surface with cross-sectional shapes including, but not limited to circular, elliptical, square, rectangular, oval, linear and ring-shaped. By judicious choice of beam "spot shape" in this manner, the practitioner can further tailor the test configuration to meet technical objectives. For example a ring-shaped spot can be configured to create a more uniform steady-state unconditioned circular beam. The angle of beam incidence to the surface can also be chosen to alter the spot shape of a beam. For example, a nominally circular beam, incident to the surface at an angle, will result in an elliptical spot shape, which could be oriented on the specimen to foster crack initiation and growth aligned to a desired plane within the material.

In addition to tailoring the shape, optical beam conditioning hardware may also be selected to tailor the flux distribution of a beam. Common configurations of interest include substantially normal (Gaussian) or substantially flat-topped (top hat) flux distributions. For example, unconditioned laser beams typically have a flux distribution bearing resemblance to a normal distribution, with high flux in the center which dies out toward the edges of the beam. By convention, the "radius" of circular Gaussian beam (for purpose of sizing the primary heat introduction zone) is defined as the distance from the center of the beam at which the flux drops to 13.5 percent ($1/e^2$) of its maximum value. A substantially flat—topped distribution can be obtained by passing a Gaussian beam through a beam conditioner, resulting in a beam that locally has substantially uniform flux across the beam, and therefore would produce a more uniform surface temperature distribution than a Gaussian beam when used to heat a specimen. Beam conditioners that transform nominally circular, Gaussian laser beams into many combinations of beam shapes and flux distributions are available commercially. Transmission of the beam by a fiber optic cable also results in a more uniform flux distribution.

The specifics of the design of energy beam sources such as lasers, and also of other specific electrical and optical components such as those mentioned above and in the following are outside the domain of the current invention as suitable devices are widely known by those skilled in the art.

For some test objectives it is useful to introduce heat such that at least one subzone of the primary heat introduction zone is heated out-of-phase relative to at least one other subzone of the same. Means to accomplish this include the use of one or more beams to irradiate subzones within the primary heat introduction zone simultaneously or at different times according to a predetermined pattern to create desired variable thermal strain states within the cycle. Where more than one beam is required, a beam splitter or more than one energy beam source may be employed. Use of a beam deflector or an articulating mount, such as a rotating or translating (x-y) table can articulate a beam (or the specimen) so that the beam is directed along a path on the surface of the specimen, movement which can include smooth operation, or sudden movement between multiple indexed locations. A moving beam can easily develop significant non-proportionality in the stress cycle. Thus the ability to direct one or more beams so it moves relative to the surface according to a pre-determined pattern gives great flexibility to the types of tests that can be devised by one skilled in the art.

A smoothly moving beam creates an infinitude of subzones being heated out-of-phase to each other. Such would be the case for a non-proportional loading test where the primary heat introduction zone is an annular zone traced by a circular beam moving around an axis. By comparing predicted and observed cycle count required to initiate or grow cracks in this manner using various test conditions, a failure theory for complex non-proportional TMF can be evaluated. By way of illustration, one skilled in the art might accomplish the same test outcome by a variety of equivalent configurations, including holding the beam stationary and rotating the specimen on a rotary table, commanding the equivalent movement on an x-y table, or again by holding the specimen stationary and articulating the beam in a circular pattern using an electro-optic beam deflector. Such will be the case with many of the embodiments presented herein.

In another application, two substantially identical subzones rotated ninety degrees from each other are heated out-of phase to create a cyclic-shear dominated TMF loading, as, for example, in two substantially linear subzones making the shape of a cross. For this purpose "substantially linear" includes but is not limited to rectangular, elliptical, or dotted-line patterns. One means to accomplish this would be to mount the specimen on a rotating table, direct an energy beam configured to irradiate a substantially linear pattern on the surface of the specimen corresponding to a first indexed position, then rotate the specimen 90 degrees about the centroid of the pattern to a second indexed position. The beam can be interrupted while rotated as required.

An alternative embodiment would be to further configure the specimen to have four holes or recesses in a square pattern, then cycle an out-of phase cross pattern as previously described on the remaining surface area between the recesses. The presence of the recesses would alter the applied stress, creating a load environment analogous to a cruciform specimen. If desired, the recesses may also be filled with a compliant insulation, to simplify thermal simulation of the test.

Increased control over the mechanical portion of the thermo-mechanical cycle can be obtained by further configuring the specimen to be gripped and loaded in a conventional mechanical test machine, thereby applying additional mechanical load to the specimen during a thermo-mechanical fatigue test.

In addition to the apparatus described above, the invention includes the test method described herein, including preparing the specimen, thermally cycling the specimen, and evaluating the test specimen for thermo-mechanical fatigue related phenomena, including use of all embodiments as described.

A further embodiment is configured to a non-destructive test on a structural component, wherein the methods described above are used to perform a thermo-mechanical fatigue test at a location on the component, further comprising reworking the specimen after testing, whereby the local damage or crack growth due to thermal cycling is removed and the surface blended or otherwise reconditioned as required to restore structural integrity. This embodiment can be applied to either new or used parts. For new and used parts, it could be useful for material and manufacturing process validation. For used parts, it could also provide information on the residual life of the part.

As can be seen, many other useful embodiments could be devised by one skilled in the art to enable testing to evaluate a wide variety of thermo-mechanical phenomena, including but not limited to thermo-mechanically induced creep, residual stress, changes in physical properties, crack initiation or crack growth in a relatively simple and cost-effective manner.

BRIEF DESCRIPTION OF THE DRAWINGS

The invention is described by way of example with reference to embodiments that are illustrated in the figures, but without thereby restricting the general object of the invention. Closely related figures have the same number, but different alphabetic suffixes.

DESCRIPTION OF EXEMPLARY EMBODIMENTS

Figure 1A:
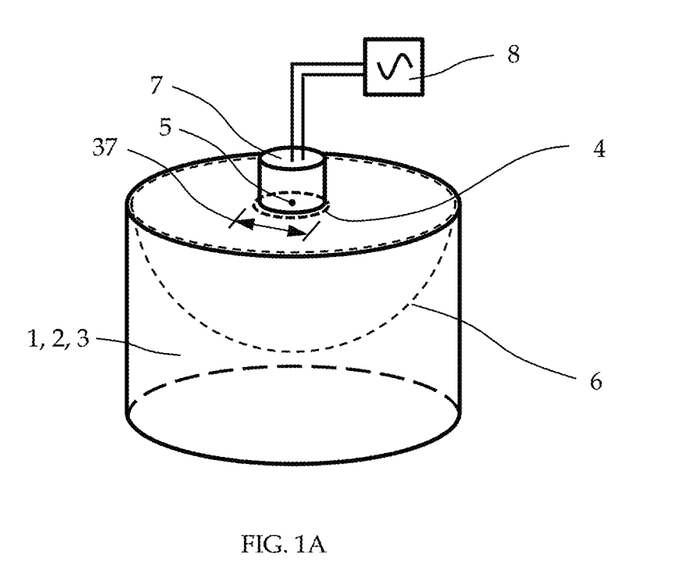
FIG. 1A shows a schematic representation of a test apparatus for assessing thermo-mechanical fatigue related phenomena in a test material.
Figure 1B:
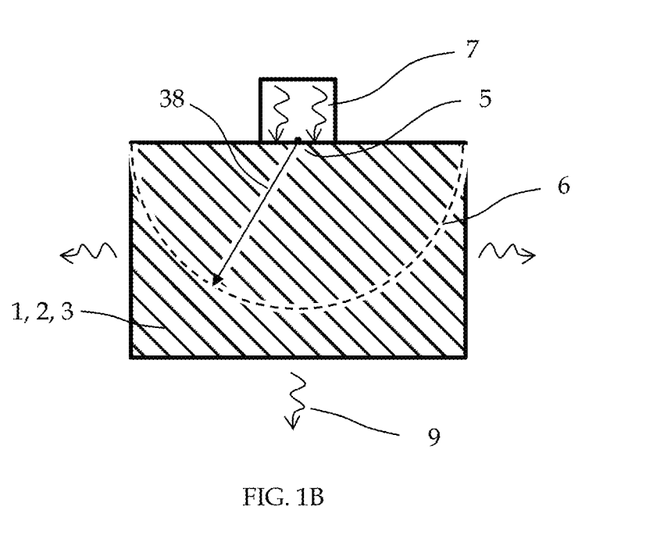
FIG. 1B shows an enlarged cross-sectional view of the same.
Figure 1C:
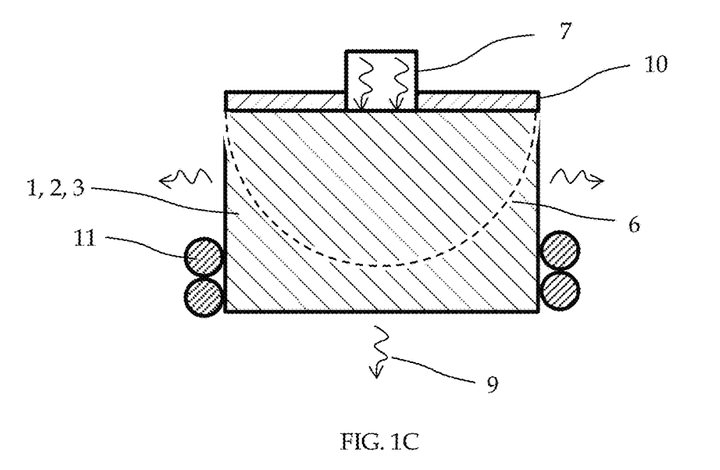
FIG. 1C illustrates use of surface insulation, and a background temperature control feature, but is otherwise identical to FIG. 1B

FIGS. 1A, 1B, and 1C show a schematic representation of a test apparatus for assessing thermo-mechanical fatigue related phenomena within a test material 1, FIGS. 1B and 1C being cross-sectional views with additional detail, and FIG. 1C illustrating additional features not shown in FIGS. 1A and 1B. The embodiment utilizes a test specimen 2 prepared of a body 3 of test material 1, with a primary heat introduction zone 4 consisting of a portion of the surface of said body 3, of a size characterized by its maximum dimension 37, and having a centroid 5. The size and shape of the body 3 is configured to substantially include a hemispherical region 6, described earlier as the fiducial hemisphere, of said test material 1 centered upon the centroid 5. For reasons already described, the ratio of the radius 38 of the fiducial hemisphere 6 to the maximum dimension 37 of the primary heat introduction zone 4 is configured to be greater than or equal to 1.2 to provide basic utility.

The embodiment further comprises means 7 for introducing heat locally through the surface of the specimen substantially within the primary heat introduction zone 4, thereby thermally cycling the material. Means 7 is generically illustrated as a heat source, shown with a variable electric power supply 8, and transmitting heat by conduction, but alternate means may include radiation or convection, and may have alternative means of interrupting, modulating, or directing heat flow to the primary heat introduction zone 4 during thermal cycling.

As shown in FIG. 1B, to further enable thermal cycling, the embodiment also includes means 9 for heat removal through a portion of the specimen surface at or beyond the spherical boundary of the fiducial hemisphere 6. The means 9 for heat removal may include natural or forced convection, radiation, and/or conduction to a heat sink (not shown).

Figure 2:
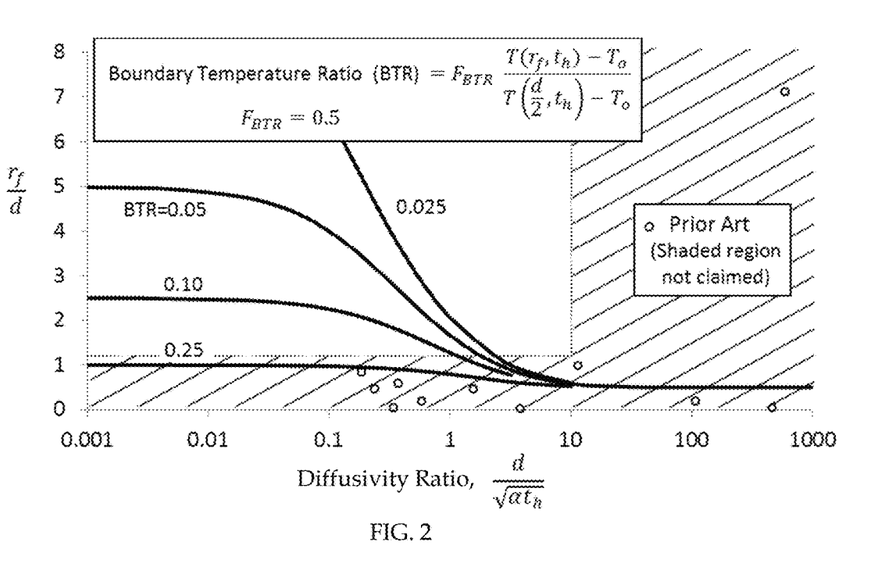
FIG. 2 shows a plot of the boundary temperature ratio (BTR) parameter as a function of dimensionless ratios involving material properties, specimen geometry, and test conditions.

FIG. 2 shows a plot of the boundary temperature ratio (BTR) parameter associated with the various test parameters using the equations and notation presented earlier. The BTR is a measure of the deviation of the local thermal distribution of the finite specimen to the corresponding spherically symmetric semi-infinite solution associated with the specimen heating cycle. Testing with a low BTR test configuration permits thickness-insensitive operation in the near-steady-state regime, facilitates accurate thermal modeling and control, and promotes efficient development of high levels of thermoelastic stress. The plot assumes a BTR factor $F_{BTR}=0.5$, which corresponds to a specimen with a uniform, constant circular flux distribution applied during the heating portion of the cycle, but which is conservative (overestimates the BTR) for a wide variety of heating scenarios as has been discussed.

On the horizontal axis, the diffusivity ratio $d/\sqrt{\alpha t_h}$ is a dimensionless parameter that represents steady state conditions at a value of zero. The radical term in the denominator may be viewed as a measure of the penetration depth associated with the heat cycle, particularly as $t_h$ becomes small. At a diffusivity ratio of approximately ten, the spherically symmetric character of the thermal solution is largely lost, and beyond ten assumes the substantially planar character associated with short pulse operation of the prior art.

Along the vertical axis, $r_f/d$ is the ratio of the fiducial radius to the primary heat introduction zone size. As has been explained, this ratio should be at least 1.2 for basic utility (corresponding to a BTR value of roughly 0.2). In many practical applications, it is useful for the $r_f/d$ ratio to be further configured to be sufficiently large that the boundary temperature ratio parameter of the test specimen at the intended test condition is below 0.1, and potentially well below this value. Note that for small spot sizes this is not a very costly requirement. For example, a nickel alloy specimen with d=1 mm (0.04 in) and a heating time $t_h=100$ sec during the cycle, would correspond to $d/\sqrt{\alpha t_h} \approx 0.05$, for which the plot indicates that use of a fiducial radius of about 2.4 mm (0.094 in) or larger would maintain a BTR less than 0.1. Running the same test with a cubic specimen measuring a mere 10 mm (0.39 in) on a side would provide a BTR below 0.05, doubling the thermal precision of the test.

The circular data points shown on the plot represent the prior art configurations previously listed in Table 1, and characterized by substantially planar thermal stress distributions. Points to the far right pertain to short pulse operation, and points along the bottom pertain to thin plate operation as discussed earlier. The shaded area of the plot represents the domain of test configurations ceded to the prior art, the unshaded region representing the domain claimed (which also extends vertically upward beyond the domain shown).

We now return to FIG. 1C, which illustrates use of optional thermal insulation 10 applied to a portion of the surface of the specimen, in this case to minimize heat loss from the specimen surface corresponding to the flat face of the fiducial hemisphere 6. It is noted that the BTR plot just described is based on equations that assume this face to be free of heat loss, though inclusion of heat loss in the absence of insulation 10 in the analysis would tend to conservatively decrease the BTR. Nevertheless, the application of insulation 10 is useful to simplify the thermal boundary conditions for thermo-mechanical analysis of the cycle, which is often associated with the evaluation phase of the method used to test the specimen. Other uses for insulation will be shown hereafter.

Also, in FIG. 1C the embodiment further includes means of introducing heat at a distributed location at or beyond the boundary of the fiducial hemisphere 6, thus raising the background temperature of the specimen during thermal cycling. While the means of introducing heat is illustrated here as a coil 11, representing either a resistance heating coil or an inductance heating coil, the application is not restricted to these means. The amount of heat input can be adjusted to control the temperature to a background value at a position remote from the primary heat introduction zone.

Figure 3A:
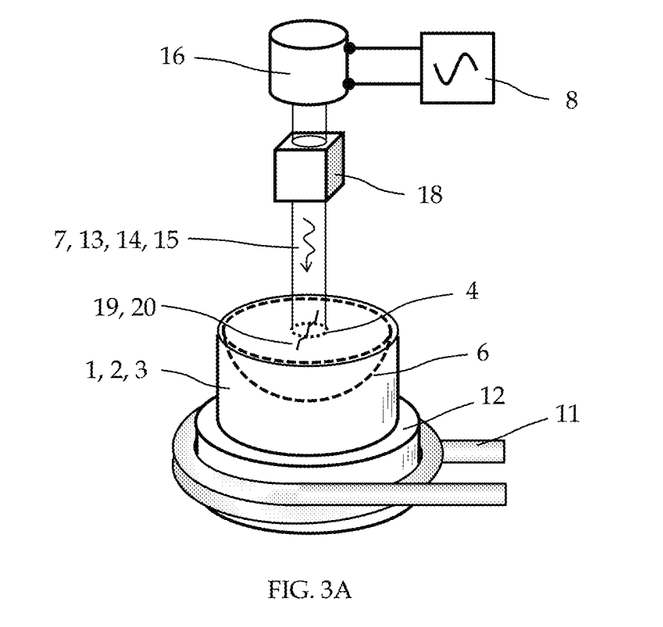
FIG. 3A shows a schematic representation of a thermo-mechanical test apparatus with an alternate configuration of the background temperature control feature, and with an energy beam for cyclic heating of the specimen.
Figure 3B:
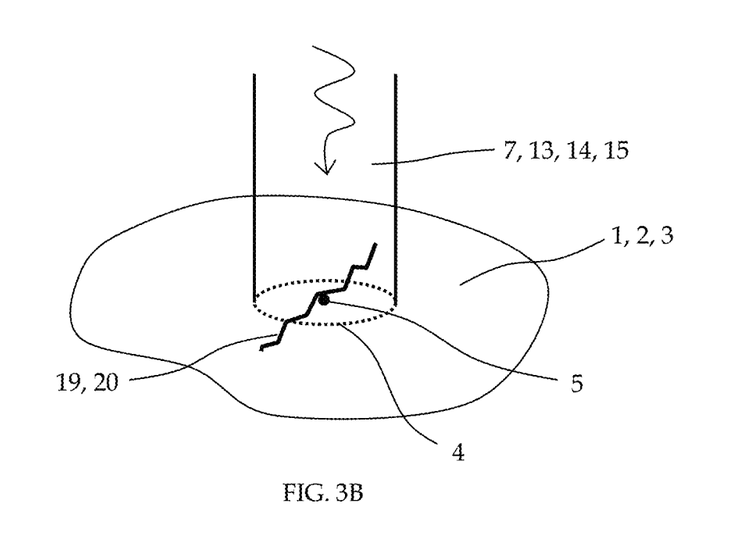
FIG. 3B shows an enlarged view of the same.

FIG. 3A and a close-up view in FIG. 3B schematically illustrate an embodiment with an alternative background temperature control arrangement, including a separate pedestal 12 heated by coil 11 which introduces heat at a distributed location beyond the fiducial hemisphere 6 by thermal conduction. Further, means 7 for introducing heat into the primary heat introduction zone 4 includes at least one energy beam 13 such as a laser 14 or an electron beam 15. Means 7 of this type can deliver high flux densities over small areas in a controlled manner, which makes them useful for the present application. In this embodiment exemplary means of cyclic heating include a beam source 16 with variable power input 8, and a beam shutter 18 by which the beam 13 is cycled to an "on" or "off" condition. As the specimen is cycled through its first and subsequent test cycles, it may be monitored and evaluated to assess thermo-mechanical fatigue related phenomena 19 within the test material, here illustrated as a crack 20. Other thermo-mechanically induced phenomena 19 of interest, include but are not limited to thermo-mechanically induced creep, residual stress, changes in physical properties, crack initiation life or crack growth rate.

Figure 3C:
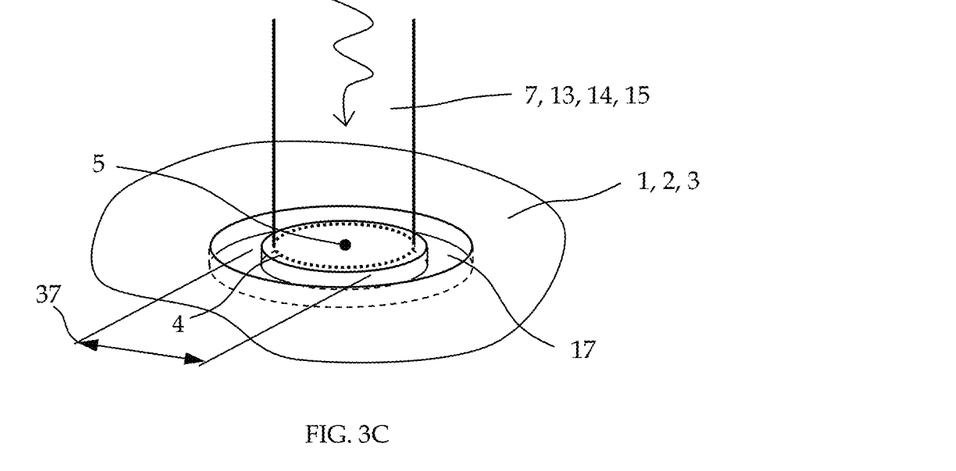
FIGS. 3C and 3D show enlarged views of alternate configurations with surface contouring with and without insulation, but otherwise identical to FIG. 3A.
Figure 3D:
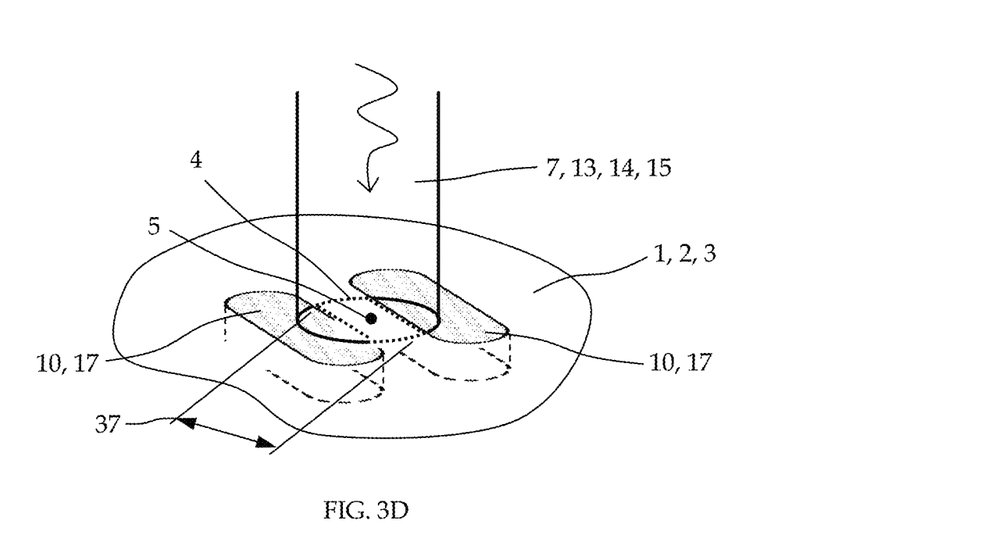

FIGS. 3C and 3D show close up views of modified embodiments of the apparatus shown in FIG. 3A illustrating the use of local surface shape modification or contouring in the vicinity of the primary heat introduction zone. In FIG. 3C, the surface is locally contoured to include recess 17 of predetermined dimensions surrounding the primary heat introduction zone 4. This technique can be used to improve the local temperature uniformity and relax the local constraint, thereby giving the practitioner additional control over the amount of thermal stress that results from a given temperature differential. It may also be useful in this situation to fill the recess 17 with compliant (flexible) insulation (not shown). The recess 17 is terminated at a predetermined depth, removing only a small fraction of the volume of the fiducial hemisphere 6.

The configuration shown in FIG. 3D illustrates the use of two parallel elongated recesses 17, filled with compliant insulation 10, wherein the insulation 10 acts to mask a portion of the specimen surface from irradiation, and the local shape of the surface fosters a substantially unidirectional thermal stress at the surface, as opposed to the biaxial stress state that would exist at the surface without the recesses 17.

Figure 4:
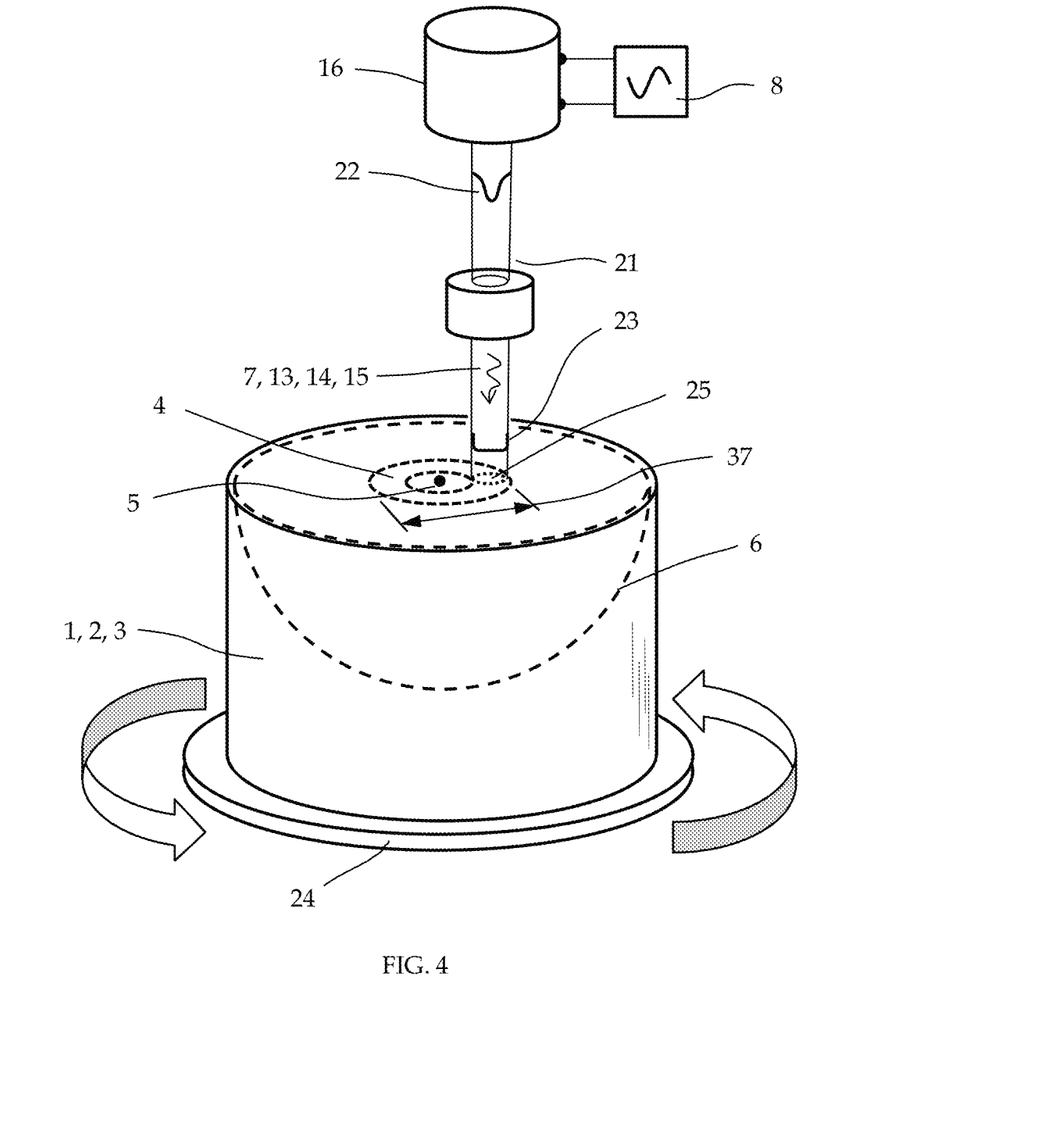
FIG. 4 shows a schematic representation of a thermo-mechanical test apparatus with a non-proportional load cycle.

FIG. 4 shows a schematic representation of a test apparatus for assessing thermo-mechanical fatigue related phenomena in a test material under an exemplary non-proportional loading condition. This embodiment further illustrates the use of a beam conditioner 21 to form at least one of the at least one energy beams to a predetermined shape and flux distribution. In this case, a circular Gaussian energy beam 22 from the energy beam source 16 is transformed into a substantially circular beam with a flat-topped flux distribution 23.

To generate an exemplary state of non-proportional loading, the primary heat introduction zone 4 is an annular zone traced by the circular beam 13 moving around the symmetry axis of the fiducial hemisphere 6. The thermal power of the beam may be either held constant, or modulated using the variable power supply 8. By comparing predicted and observed cycle count required to initiate or grow cracks in this manner using various test conditions, a failure theory for complex non-proportional TMF can be evaluated in comparison to the test data. While many equivalent mechanisms could produce a similar motion of the beam 13 relative to the specimen 3, the configuration shown employs a rotating table 24. Over time, the location of the subzone 25 being heated at any given time moves around the annular zone, defining an infinite number of different subzones 25 on the surface of the part within the primary heat introduction zone 4, each of which is heated out-of-phase from the others. This relative motion is thus an exemplary means for introducing heat that is configured such that at least one subzone of the primary heat introduction zone is heated out-of-phase relative to at least one other subzone of the same.

Figure 5:
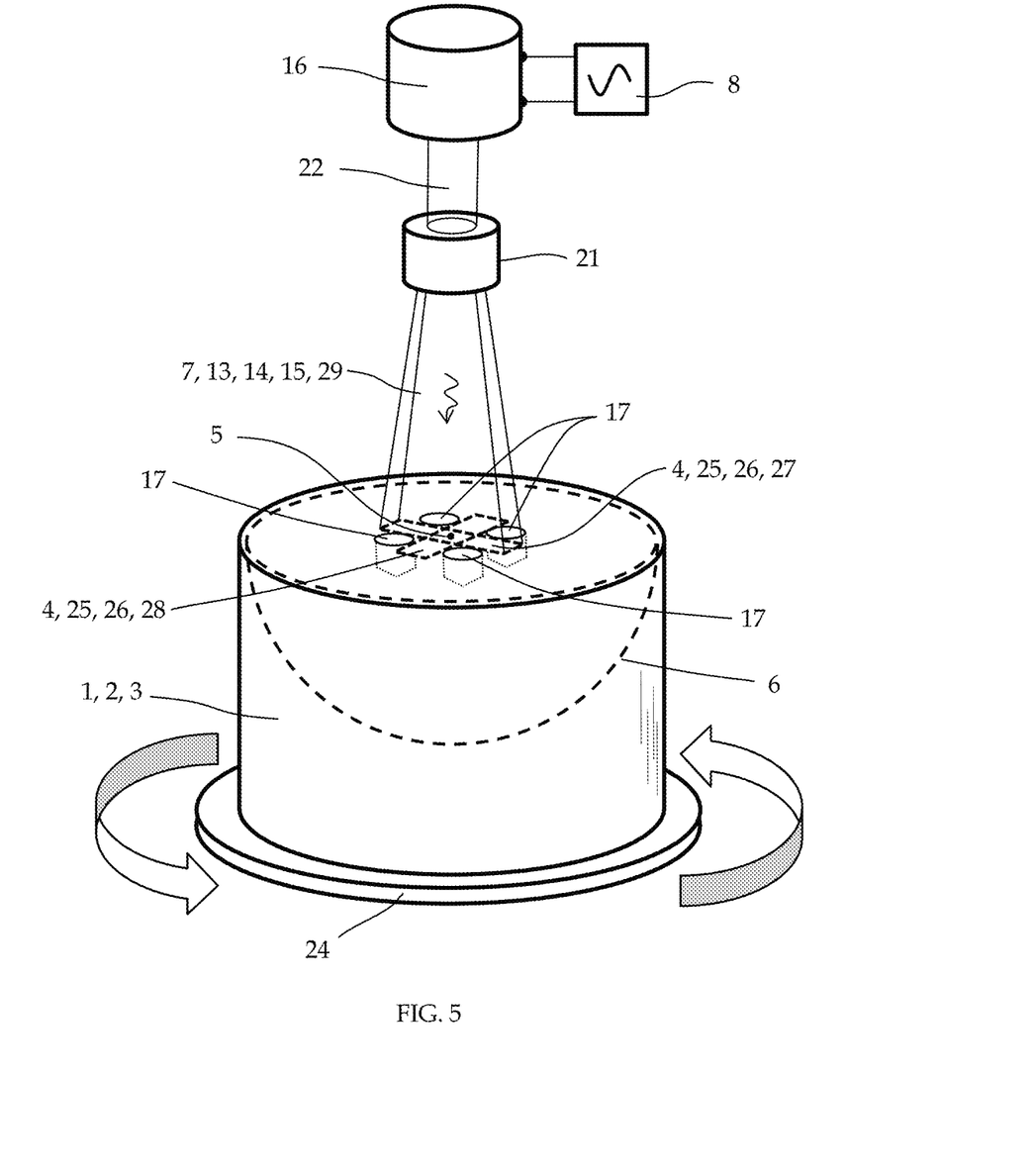
FIG. 5 shows a thermo-mechanical test apparatus operating with a shear-dominated load cycle.

FIG. 5 Illustrates an apparatus wherein two substantially identical subzones 25 rotated ninety degrees from each other are heated out-of phase to create a cyclic-shear dominated TMF loading, as, for example, in two substantially linear subzones 26 making the shape of a cross. For this purpose "substantially linear" includes but is not limited to rectangular, elliptical, or dotted-line patterns. One means to accomplish this would be to mount the specimen on a rotating table 24, direct an energy beam 13 through a beam conditioner 21 to create a beam with a substantially linear beam shape 29, thereby irradiating a substantially linear subzone 26 on the surface of the specimen corresponding to a first indexed position 27, then rotate the specimen 90 degrees about a common axis to a second indexed position 28. The beam can be interrupted or modulated during rotation, or at other intervals as required using the variable power supply 8.

An optional feature also shown is to further configure the specimen to have four recesses 17 shown as circular holes in a square pattern, then cycle an out-of phase cross pattern as previously described on the remaining surface area between the recesses 17. The presence of the recesses 17 alters the applied stress, creating a load environment analogous to a cruciform specimen. The recesses 17 may be terminated at a predetermined depth as shown, removing only a small fraction of the volume of the fiducial hemisphere 6. If desired, the recesses 17 may also be filled with a compliant insulation (not shown), to simplify thermal simulation of the test.

Figure 6:
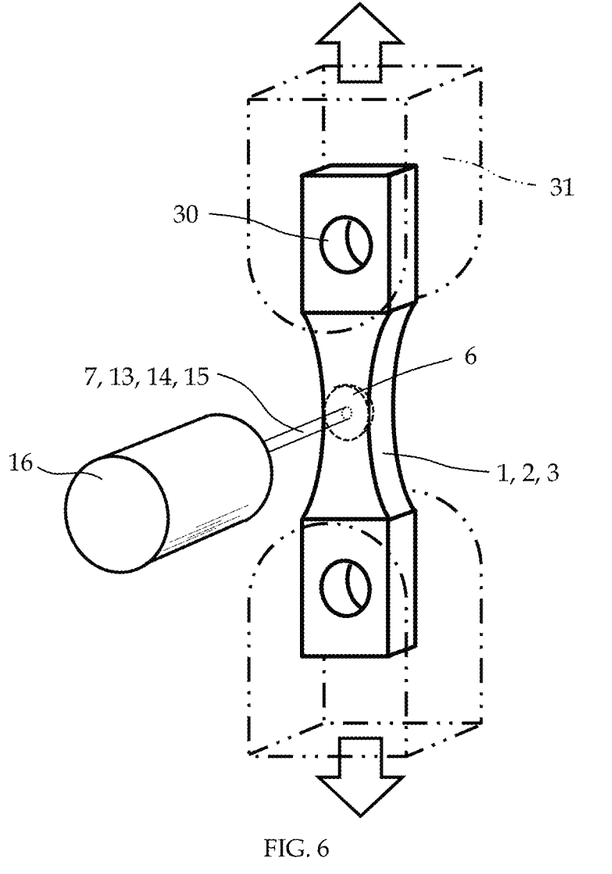
FIG. 6 shows a schematic representation of a thermo-mechanical test apparatus with the specimen further configured to be gripped and loaded in a conventional mechanical test machine.

As illustrated in FIG. 6, increased control over the mechanical portion of the thermo-mechanical cycle can be obtained by further configuring the specimen with end grips 30 or equivalent means to be gripped and loaded in a conventional mechanical test machine, represented here by the devises 31 of a uniaxial test machine but equally applicable to biaxial, bending, or other modes of loading, thereby applying additional mechanical load to the specimen 2 during a thermo-mechanical fatigue test.

Figure 7:
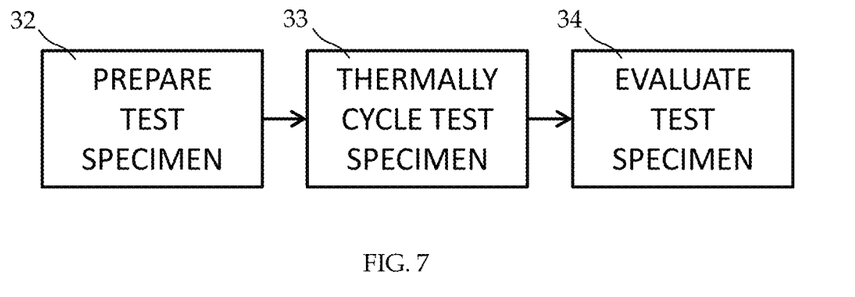
FIG. 7 shows a flowchart of a test method for assessing thermo-mechanical fatigue related phenomena in a test material.

FIG. 7 shows a flow chart summarizing the test method associated with use of the embodiments thus far discussed, which includes preparing the specimen 32, thermally cycling the specimen 33 through at least one test cycle, and evaluating the specimen 34 for thermo-mechanically fatigue related phenomena.

The use of a flow chart should not be construed to limit the order of activities represented to a strict sequential order. For example, data for the evaluation phase 34 may be gathered at any time during the process, from recording the dimensions of the specimen configuration as it is during specimen preparation 32, to gathering temperature, deflection, ultrasound, crack length, or other data during thermal cycling 33 using methods common in the art. Further, embodiments of the test method must be construed to broadly include the use of all features of the apparatus embodiments heretofore described or any combination thereof.

Figure 8A:
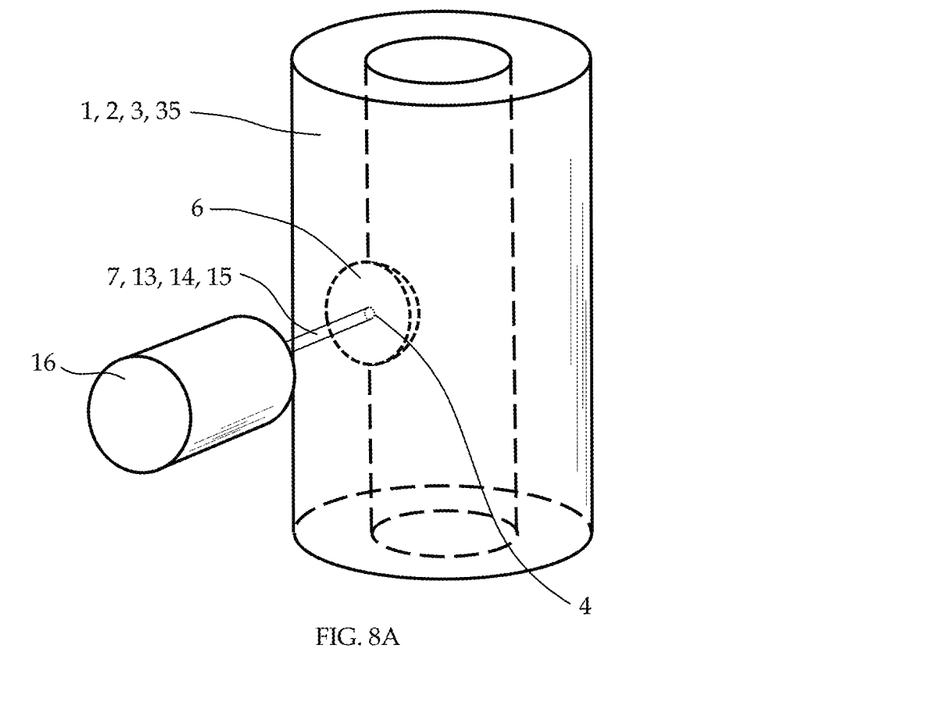
FIG. 8A shows a thermo-mechanical test apparatus configured to a non-destructive test of a structural component.
Figure 8B:
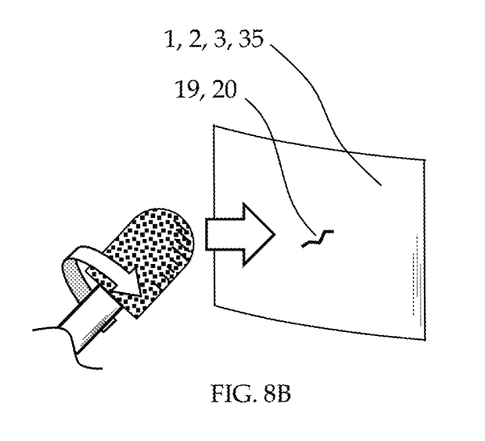
FIG. 8B shows an enlarged view of the surface of the specimen after the test, illustrating removal of cracking or other damage.
Figure 8C:
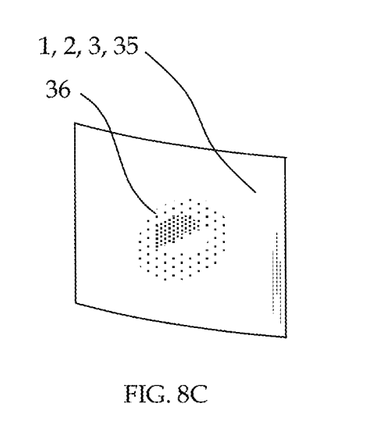
FIG. 8C shows the reconditioned test location.

FIGS. 8A, 8B and 8C illustrate a further embodiment configured to a non-destructive test on a component 35, wherein the methods described above are used to perform a thermo-mechanical fatigue test at a location on the component 35. This embodiment further comprises reworking the component 35 after testing as portrayed in an enlarged view of the surface in FIG. 8B, whereby the region containing TMF related phenomena 19, such as local damage or crack growth 20 due to thermal cycling, is removed by grinding or other suitable process, and the surface blended or otherwise reconditioned as required to restore functionality and structural integrity. In FIG. 8C, the reconditioned zone 36 is portrayed as a blended-out portion of the surface. Some components 35 might require additional surface processing such as shot peening or applying a surface coating specific to the component (not shown). This embodiment can be applied to either new or used components. For both new and used components, it could be useful for material and manufacturing process validation. For used components, it could also provide information on the residual life of the component.

Although the present invention has been described in considerable detail with reference to certain preferred versions thereof, alternate configurations and arrangements can be easily devised by one skilled in the art to enable testing to evaluate a wide variety of thermo-mechanical fatigue related phenomena, including but not limited to thermo-mechanically induced creep, residual stress, changes in physical properties, crack initiation or crack growth in a relatively simple and cost-effective manner. Therefore, the spirit and scope of the appended claims should not be limited to the description of the preferred versions contained herein. The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

LIST OF REFERENCE SYMBOLS

1 Test material
2 Test specimen
3 Body of test material
4 Primary heat introduction zone
5 Centroid of primary heat introduction zone
6 Hemispherical region, referred to as fiducial hemisphere
7 Means for introducing heat to a portion of the surface of the specimen (heat source)
8 Variable power supply
9 Means of heat removal
10 Insulation
11 Heating coil
12 Pedestal
13 Energy beam
14 Laser beam
15 Electron beam
16 Energy beam source
17 Recess
18 Beam Shutter
19 Thermo-mechanically induced phenomena
20 Fatigue crack and growth thereof
21 Beam conditioner
22 Unconditioned energy beam (circular, Gaussian)
23 Energy beam conditioned to have a substantially flat-top flux distribution where it meets the specimen surface.
24 Rotating table
25 Subzone of primary heat introduction zone
26 Substantially linear subzone
27 First indexed position
28 Second indexed position
29 Energy beam conditioned to have a substantially linear shape
30 End grip for attachment to conventional mechanical test machine
31 Attachment hardware (shown as clevis) pertaining to conventional mechanical test machine
32 Specimen preparation phase of test method
33 Thermal cycling phase of test method
34 Evaluation phase of test method
35 Component
36 Reconditioned zone on surface of component
37 Maximum dimension of the primary heat introduction zone, d
38 Radius of hemispherical region, $r_f$

The invention claimed is:

1. A test apparatus for assessing thermo-mechanical fatigue related phenomena within test material, comprising:
   (a) a test specimen having a surface, comprising,
      (i) a body of said test material, and
      (ii) a primary heat introduction zone consisting of a portion of the surface of said body, of a size characterized by its maximum dimension, and having a centroid, wherein the size and shape of said body is configured to substantially include a hemispherical region of said test material centered upon said centroid, and having a radius, from said centroid to a spherical boundary pertaining to said hemispherical region, wherein the ratio of said radius to said maximum dimension is at least 1.2, and
   (b) means for introducing heat locally through the surface of the specimen substantially within said primary heat introduction zone, thereby thermally cycling the material, wherein said heat introduction results in a diffusivity ratio that does not exceed ten; and
   (c) means for heat removal from the surface of the specimen at or beyond said spherical boundary of said hemispherical region.

2. The apparatus according to claim 1 wherein said ratio between said radius and said maximum dimension is further constrained to be sufficiently large that said test specimen has a boundary temperature ratio parameter at intended test conditions that is less than 0.1.

3. The apparatus according to claim 1 further comprising thermal insulation applied to a portion of the surface of said specimen.

4. The apparatus of claim 1 wherein, said apparatus further comprises means for introducing heat in a distributed manner to a portion of the specimen surface or volume beyond said boundary of said hemispherical region, thereby heating said specimen remotely to an increased background temperature.

5. The apparatus according to claim 1 wherein at said means for introducing heat includes at least one energy beam.

6. The apparatus of claim 5 wherein:
   (a) said energy beam includes a laser, and
   (b) said apparatus further comprises means for introducing heat in a distributed manner to a portion of the specimen surface or volume beyond the boundary of said hemispherical region, thereby heating the specimen remotely to an increased background temperature.

7. The apparatus according to claim 5 further comprising a beam conditioner to form at least one of said at least one energy beams to a predetermined shape and flux distribution.

8. The apparatus of claim 1 wherein the shape of the specimen surface in the vicinity of the primary heat introduction zone is locally contoured to a predetermined shape thereby further tailoring the desired thermo-mechanical fatigue cycle occurring in the material as it is cyclically heated.

9. The apparatus of claim 1, wherein said means for introducing heat are configured such that at least one subzone of the primary heat introduction zone is heated out-of-phase relative to at least one other subzone of the same.

10. The apparatus of claim 9, wherein the subzones heated out-of-phase comprise two substantially identical subzones rotated ninety degrees from each other about a common axis.

11. The apparatus of claim 1, wherein said specimen is further configured with means to be gripped and loaded in a conventional mechanical test machine, thereby applying additional mechanical load to the specimen during testing.

* * * * *